US010312063B2

(12) United States Patent
Leszczyszyn et al.

(10) Patent No.: US 10,312,063 B2
(45) Date of Patent: Jun. 4, 2019

(54) ELUATE ANALYSIS AND COLLECTION

(71) Applicant: Malvern Panalytical Limited, Worcestershire (GB)

(72) Inventors: Oksana Iryna Leszczyszyn, Worcestershire (GB); Paul G. Clarke, Worcestershire (GB); Mark Nicholls, Worcestershire (GB); E. Neil Lewis, Worcestershire (GB)

(73) Assignee: Malvern Panalytical Limited, Malvern, Worcestershire (GB)

( * ) Notice: Subject to any disclaimer, the term of this patent is extended or adjusted under 35 U.S.C. 154(b) by 259 days.

(21) Appl. No.: 14/783,826

(22) PCT Filed: Mar. 12, 2014

(86) PCT No.: PCT/GB2014/050736
§ 371 (c)(1),
(2) Date: Oct. 9, 2015

(87) PCT Pub. No.: WO2014/140570
PCT Pub. Date: Sep. 18, 2014

(65) Prior Publication Data
US 2016/0146766 A1  May 26, 2016

(30) Foreign Application Priority Data

Mar. 14, 2013  (GB) .................................. 1304631.3
Oct. 15, 2013  (GB) .................................. 1318248.0

(51) Int. Cl.
*G01N 30/00*  (2006.01)
*G01N 30/74*  (2006.01)
(Continued)

(52) U.S. Cl.
CPC ........ *H01J 37/32807* (2013.01); *B01D 15/10* (2013.01); *C07K 1/16* (2013.01);
(Continued)

(58) Field of Classification Search
CPC ...... B01D 15/08; B01D 15/10; B01D 15/247; C07K 1/16; G01N 15/1404;
(Continued)

(56) References Cited

U.S. PATENT DOCUMENTS 5,250,186 A * 10/1993 Dollinger ........... G01N 15/0205
                                                    210/198.2
5,541,420 A   7/1996 Kambara
(Continued)

FOREIGN PATENT DOCUMENTS

EP        0461382        12/1991
WO        WO-92/07244     4/1992
(Continued)

OTHER PUBLICATIONS

Kenny, A et al. (1991) "An Advanced Protein Chromatography Detector," *American Laboratory* 23(8): 4 pages.
(Continued)

*Primary Examiner* — Maureen Wallenhorst
(74) *Attorney, Agent, or Firm* — Morrison & Foerster LLP

(57) ABSTRACT

The invention relates to analyzing and controlling collection of liquid eluate output from a separation process, in particular by use of a measure of suspended material in the eluate based on a light scattering detection method. Exemplary embodiments include a method of controlling collection of a sample of a liquid eluate output from a separation process. The method includes exposing the liquid eluate to light from a light source; detecting light from the light source scattered by suspended material in the eluate at a detector; and beginning and ending collection of the sample when a measure of the suspended material derived from the detected scattered light enters and leaves a predetermined range.

15 Claims, 4 Drawing Sheets

(51) Int. Cl.
  *G01N 30/82* (2006.01)
  *B01D 15/10* (2006.01)
  *C07K 1/16* (2006.01)
  *G01N 15/14* (2006.01)
  *H01J 37/32* (2006.01)
  *G01N 27/447* (2006.01)
  *F16B 7/04* (2006.01)
  *G01N 27/453* (2006.01)
  *G01N 21/53* (2006.01)
  *G01N 33/68* (2006.01)
  *B01D 15/24* (2006.01)
  *G01N 30/02* (2006.01)

(52) U.S. Cl.
  CPC ....... *F16B 7/0406* (2013.01); *G01N 15/1404* (2013.01); *G01N 27/44739* (2013.01); *G01N 27/453* (2013.01); *G01N 30/0005* (2013.01); *G01N 30/74* (2013.01); *G01N 30/82* (2013.01); *H01J 37/32357* (2013.01); *B01D 15/247* (2013.01); *G01N 21/532* (2013.01); *G01N 27/44721* (2013.01); *G01N 33/68* (2013.01); *G01N 2030/027* (2013.01); *H01J 2237/334* (2013.01); *Y10T 403/66* (2015.01)

(58) Field of Classification Search
  CPC ....... G01N 2030/027; G01N 27/44721; G01N 27/44739; G01N 27/453; G01N 30/0005; G01N 30/74; G01N 30/82; G01N 21/47; G01N 21/53; G01N 21/532; G01N 33/68; Y10T 436/117497; Y10T 436/12; Y10T 436/25375; Y10T 436/255
  USPC ..... 436/52, 55, 86, 161, 164, 172, 177, 178, 436/901; 422/82.05, 82.08, 82.09, 70, 422/527, 537; 204/452, 602; 210/656, 210/96.1; 356/338; 530/417
  See application file for complete search history.

(56) References Cited

U.S. PATENT DOCUMENTS

| | | | |
|---|---|---|---|
| 7,630,076 B2* | 12/2009 | Kalonia | G01N 21/05 356/338 |
| 9,146,192 B2* | 9/2015 | Some | G01N 21/47 |
| 2001/0027949 A1 | 10/2001 | Safir et al. | |
| 2013/0303732 A1* | 11/2013 | Hewig, III | C07K 16/065 530/387.1 |

FOREIGN PATENT DOCUMENTS

| WO | WO-2009/075764 | 6/2009 |
|---|---|---|
| WO | WO-2011/140345 | 11/2011 |

OTHER PUBLICATIONS

Moritz, Ralf et al. (Jun. 2003). "Mass-Based Fraction Collection of Crude Synthetic Peptides in Analytical and Preparative Scale," *Journal of Biomolecular Techniques* 14(2): 136-142.

Lago, P et al. (Jul. 1993). "A Quasielastic Light Scattering Detector for chromatographic Analysis," *Review of Scientic Instruments* 64(7): 1797-1802.

International Search Report and Written Opinion dated Oct. 13, 2014 directed towards PCT Application No. PCT/GB/2014/050736; 8 pages.

\* cited by examiner

ELUATE ANALYSIS AND COLLECTION

CROSS-REFERENCE TO RELATED APPLICATIONS

This application is a U.S. National Phase patent application of PCT/GB2014/050736, filed on Mar. 12, 2014, which claims priority to GB Application No. 1318248.0, filed Oct. 15, 2013, and GB Application No. 1304631.3, filed on Mar. 14, 2013, each of which is hereby incorporated by reference in the present disclosure in its entirety.

FIELD OF THE INVENTION

The invention relates to analysing and controlling collection of liquid eluate output from a separation process, in particular by use of a measure of suspended material in the eluate based on a light scattering detection method.

BACKGROUND

Biotherapeutic drugs, which may be defined as being derived from living organisms, and includes both proteins and DNA, comprise an important class of medicines that have attracted significant interest from both academic and commercial environments Examples of such drugs include monoclonal antibodies (mABs), Human growth hormone (hGH), insulin and glucagon. In the last decade in particular, a remarkable increase in the research, development and clinical use of biotherapeutic drugs for the treatment of a wide range of diseases, including various cancers, rheumatoid arthritis and multiple sclerosis, has been observed. Many of the currently approved mAB-based drugs (as approved by the US Food and Drug Administration) have been approved in the past five years.

Strict regulatory guidelines require that biotherapeutic drug products are clinically safe. This can significantly lengthen the time before a drug becomes available on the market. Product-specific requirements are, in part, satisfied through full characterisation of the molecular properties, solution behaviour and stability of the biotherapeutic drug formulation and, ultimately, by the demonstrable manufacture of a pure, homogeneous product.

One of the main challenges associated with the production of pure and homogenous biotherapeutic drugs is the formation of aggregates. An aggregate may be defined as an assembly of n monomers (where n>1), a monomer being defined as the most basic, non-divisible, unit of an intact protein molecule. Although natural aggregates, in the form of dimers, trimers and other higher order associations, can occur in some proteins and are essential for proper physiological function, for example in Thyroglobulins, Superoxide distumases and Aldolases; for mABs and other protein-based drugs the formation of aggregates is not required for drug function and instead can adversely affect their role as biotherapeutic agents. The immunogenic potency, i.e. the degree to which a molecule (biological or otherwise) is able to elicit an immunological response, of large protein aggregates that may be made up of several million protein molecules has been widely documented, for example via draft FDA guidance on immunogenicity assessment for therapeutic products issued in 2013 (available from www.fda.org). Whilst potency is a desired attribute for any therapeutic drug, the inherent heterogeneity of aggregate structures is problematic from manufacturing and quality control (QC) perspectives. Presently, the currently limited understanding of aggregate formation does not allow for the controlled and reproducible assembly of homogenous high-order aggregates and, thus, the intensity of immunogenic response cannot be accurately correlated with such molecules. Consequently, FDA guidelines currently recommend that that the presence of aggregates in biotherapeutic drug products are minimised, not only at manufacture but for the duration of the product's shelf-life.

The primary experimental strategy for the production of a highly pure biotherapeutic product centres on the physical separation, or otherwise known as fractionation, of the protein monomer from its aggregated counterparts within a mixture. Fractionation is principally achieved through liquid chromatography, a technique that uses a liquid flow through specifically functionalised columns to influence the elution of protein molecules by exploiting a range of molecular properties, such as size, binding affinity and electrostatic charge. Since the monomer and aggregates do not share the same molecular properties, their elution from functionalised columns is temporally differentiated, and isolation of the purified monomer is possible. Clearly, the analytical power in this technique is only truly realised when it is coupled with a detector that can monitor and visualise the fractionated species eluting over time. Examples of various techniques that are either currently used, or could be used, as liquid chromatography detectors are summarised in Table 1 on the following page.

TABLE 1

A summary of properties of various detectors coupled with existing liquid chromatography systems.

| Detector | Property | Information | Advantage | Disadvantage | Used to control fraction collector |
|---|---|---|---|---|---|
| Ultraviolet (UV) | Absorbance of light at a specific wavelength | Concentration if detector is calibrated & extinction coefficient known | Inexpensive; widely applicable for protein analysis | No identity information; doesn't respond to structural changes | Y |
| Refractive Index (RI) | Refraction of light compared to reference | | Inexpensive | Signal instability with buffer changes or environmental condition e.g. salt gradients and temperature | Y |
| Fluorescence | Emission of light at a specific wavelength | | Inexpensive; sensitive | Requires fluorescent probe; small linear range due to sensitivity | Y[1] |
| Mass Spectrometry | Mass to charge ratio | Molecular mass | Identification of eluting species positively | Expensive; destructive; not compatible with excipients; | Y[2] |

TABLE 1-continued

A summary of properties of various detectors coupled with existing liquid chromatography systems.

| Detector | Property | Information | Advantage | Disadvantage | Used to control fraction collector |
|---|---|---|---|---|---|
| (MS) | | | confirmed | requires compatible buffer; cannot work at formulation concentrations; ionisation can disrupt weakly associated; automated detection of intact proteins not available | |
| Nuclear Magnetic Resonance (NMR) | Probing electromagnetic field of nuclei with NMR-active spin | 3D structure | Detailed structural information | Expensive; Large footprint; Long analysis times; Labour intensive; Requires experienced person for data interpretation; non-continuous detection; mainly used for small molecules; required deuterated solvents and sample modification; not compatible with formulation excipients | N |
| Elemental analysis (AAS/ICP-OES) | Absorbance of light at discrete wavelengths by free atoms in a gaseous state | Concentration of element under study | Specific way to follow elution of target protein if metal binding | Destructive; Usually used in conjunction with concentration detector; unless metal stoichiometry known then protein species cannot be identified | N |
| Evaporative light scattering | Light scattered by molecule in gas phase | Mass | Relatively inexpensive | Not applicable for protein applications as technique requires gas phase | Y |

Notes:
[1]See for example U.S. Pat. No. 5,541,420
[2]See R. Moritz and N. O'Reilly, *J Biomol Tech.* 2003 June; 14(2): 136-142

Ultraviolet (UV) detectors are common amongst detectors coupled with liquid chromatography systems for the purpose of profiling protein mixtures for isolation or purification of their components. This is largely due to their cost-effectiveness and wide applicability for protein samples. UV detectors capitalise on a natural and quantifiable phenomenon common to all proteins arising from chromophores: functional groups that are able to absorb light at specific wavelengths. In proteins, for example, the peptide bond absorbs light at 215 nm and the aromatic group on certain amino acids absorbs at 280 nm. No modification is therefore required to be made to the proteins to determine their presence under UV light, and analyses can occur with the protein unmodified.

Signal responses from refractive index (RI) and fluorescence detectors are also quantifiable, but their use in protein purification applications is limited due to signal instability with changes in buffer components and the need for a fluorescent probe, respectively. Concentration information is inherent in the data from all three types of detectors, but no further information confirming the identity of the fractionated species can be extracted from such measurements. Such confirmation would require the implementation of additional offline methods, which contribute significantly to the total analysis and handling times and, correspondingly, decrease efficiency and profitability.

To provide identity information, mass spectrometry (MS) and nuclear magnetic resonance (NMR) technologies in tandem with liquid chromatography systems may be used. However, the additional information obtained through these techniques comes at a price, including increased equipment and running costs and prolonged analysis times. MS and NMR also suffer from sample-specific issues, where the excipients used in biopharmaceutical formulations are frequently incompatible with either technique, as are the concentrations of the protein within. Whether MS accurately reflects the species contained within the original solution is another critical issue for consideration in biopharmaceutical analyses. Since this technique relies on the ionisation of charged groups, the likelihood of observing a given species is directly correlated with the accessibility of these charged sites—which may or may not be the same for two aggregate particles of the same mass—and, furthermore, the ionisation itself may also cause dissociation of weakly associated molecules.

Following successful fractionation of a biopharmaceutical or protein/aggregate mixture, the next consideration is isolation of the fractionated protein monomer. UV, RI, fluorescence and mass spectrometer technologies that facilitate the isolation of fractionated species by controlling a fraction collector are commercially available. This signal-based fraction collection is largely accomplished through user-set parameters that define specific conditions during which a particular fraction should be collected. Such conditions may for example relate to changes in peak slope or absolute signal above a threshold value. The disadvantage of using UV- or RI-directed fraction collection for biopharmaceutical mixtures is that these detectors lack the ability to discriminate between a protein monomer and its aggregates. For example, there is no discernable difference in the signal response for 10 individual monomers or an aggregate composed of 10 monomers. This means that the efficiency of the peak fractionation, i.e. the ability to identify where peaks begin and end in both baseline resolved and unresolved situations, is solely based on the ability to detect changes in the intensity of the resultant peaks during real-time measurements of the phenomenon under observation.

More selective fraction collection based on species identity is possible with mass spectrometry, where a given fraction is collected based on the detection of a particular mass. However, it is important to remember that when looking at intact proteins that the observed species are presented as a mass to charge ratio; therefore, as far as the MS detector is concerned a species of mass 100 and charge of +10 would be the same as a species of mass 10 and charge of +1. No real-time deconvolution of such data is currently possible. Even when looking at peptide fingerprints, such selective fractionation excludes all information from other molecules and as a result does not allow the user to effectively minimise contamination of the fraction from other closely eluting species. Similar drawbacks are applicable for selective fractionation based on fluorescence or elemental analyses.

Ensuring a high purity product at maximum yield is a specific manufacturing challenge faced by the biopharmaceutical industry, on both small and large scales, which is required to meet stringent regulatory demands whilst maintaining profitability. Concomitantly, the demand for technologies that detect, characterise and quantify aggregates, both during and post-manufacture, has increased and manufacturers of scientific instrumentation have duly responded. The benefits of using detectors for online monitoring in polymer manufacture have been recognised and implemented with the optimisation tool ACOMP (automatic continuous online monitoring of polymerisation reaction, as described for example in U.S. Pat. Nos. 6,052,184 and 6,653,150). This tool aims to increase efficient production of a polymerisation reaction by adjusting variables, such as pressure, temperature and reagent concentrations, based on the feedback from real-time analyses of several parameters. However, no technology currently available offers real-time, signal-based fraction collection or identity-based selective fractionation. All existing technologies for analysis of protein/aggregate mixtures require some degree of user intervention for data processing, and none currently allow for automated, software-driven identification of monomer and aggregate peaks or corresponding fractions.

It is an object of the invention to address one or more of the above mentioned problems.

SUMMARY OF THE INVENTION

In accordance with a first aspect of the invention there is provided a method of controlling collection of a sample of a liquid eluate output from a separation process, the method comprising:
exposing the liquid eluate to light from a light source;
detecting light from the light source scattered by suspended material in the liquid eluate at a detector; and
beginning and ending collection of the sample when a measure of the suspended material derived from the detected scattered light enters and leaves a predetermined range.

An advantage of the invention is that the use of scattered light can provide a more accurate indication of when a particular desired property of an eluate, such as protein aggregate size, is within a desired range. The method also allows for a more objective measurement, which reduces the need for a separate calibration to be carried out for determining the range to be used, thereby improving efficiency of sample collection particularly for small batch processes where the analyte used as a feedstock may be of high cost.

The measure of suspended material may be a measure of intensity of the detected scattered light, obtained for example using a static light scattering (SLS) technique. Static light scattering is a particular preferred technique because it is very suitable for measurements of small, i.e. nanometer-scale, dispersed particles such as proteins, and results in a measure of molecular weight. Detection of scattered light at angles of around 90° from the incident light is generally preferred, although other angles may be used.

The measure may be a measure of a rate of change of intensity of the detected scattered light. In the case of a rate of change of intensity, collection may for example begin when the rate of change increases above a predetermined value and end when the rate of change falls below the predetermined value.

The measure of the suspended material may include a measure of size of particles of the suspended material determined from the detected scattered light, which may be obtained using one or both of a static light scattering and dynamic light scattering (DLS) technique. Use of a dynamic light scattering technique can, for example, provide an indication of the hydrodynamic radii of particles of the suspended material based on the detected scattered light. DLS, also known as photon correlation spectroscopy or quasi-elastic light scattering, does not measure the molecular weight directly, but indirectly through distinguishing between monomer proteins and aggregates from their difference in hydrodynamic size.

The measure of the suspended material may be a ratio, or inverse ratio, of intensity of the detected scattered light to the measure of size of particles of the suspended material.

The measure of the suspended material may include a measure of intensity of light scattered by the suspended particles and a measure of concentration of the suspended material in the eluate, the measures of intensity of scattered light and concentration being combined to obtain the measure of the suspended material. An advantage of this approach is that by combining two different techniques for determining concentration and scattered light intensity, both of which may be obtained optically, a measure of molecular weight of the suspended compound can be determined that can be obtained in real time and on a flowing liquid sample with a changing concentration. This makes the invention highly suitable for identification and isolation of components of the eluate.

The measure of concentration may be obtained by determining the refractive index of the eluate. Measurements involving refractive index are less preferred because the measure is more dependent on environmental conditions and can be susceptible to signal instability.

Other alternatives for measuring concentration may include UV absorption or fluorescence, atomic absorption spectroscopy or evaporation light spectroscopy.

With the light source being termed a first light source and the detector a first detector, in some embodiments the liquid eluate may be being further exposed to light from a second light source, the measure of concentration being derived from a response from the eluate to the light from the second light source detected by a second detector. The first and second light sources may be arranged to illuminate a common sample volume, or alternatively may be arranged to illuminate different portions of a flow line containing the liquid eluate.

The second light source may be an ultraviolet light source.

The response from the eluate may be fluorescence in response to light from the second light source or alternatively may be attenuation of light from the second light source detected by the second detector.

The measure of the suspended material may be a measure of size of particles of the suspended material obtained by dividing the measure of intensity of scattered light by the measure of concentration. This simple step to determine the measure of size, which relates closely to molecular weight in the case of protein suspensions, can be performed very quickly and therefore effectively in real time on a flowing sample.

Either fluorescence or absorption may be used to determine the concentration of a compound, such as a protein, in the liquid dispersion. In applications involving separation of proteins in an eluate, light absorbance is generally preferred unless the proteins in question have an ability to fluoresce under UV light.

In alternative embodiments the second light source and detector are configured to detect a refractive index of the liquid dispersion. As mentioned above, measurements involving refractive index are less preferred because the measure is more dependent on environmental conditions and can be susceptible to signal instability.

Where the first and second light sources are arranged to illuminate different portions of a flow line containing the liquid dispersion, either the determined concentration or the determined measure of intensity of scattered light may be time shifted according to the time taken for a sample to flow between the different portions of the flow line before the step of combining to determine the measure of size. An advantage of illuminating different portions of the liquid dispersion is that the apparatus required for taking the different measurements does not need to be integrated, and the difference in illuminated positions can be accommodated by time shifting one of the measurements, for example by applying a time delay to the sample measurement that is taken first. An advantage of taking the measurements on a common sample volume is that time shifting the measurement data is not required, and any decisions based on the measurements can therefore be taken more quickly, resulting in less wasted material.

The start of eluate collection may, for example be determined when the size measure rises above a first predetermined level, indicating the presence of particles of a compound having a chosen size, and ended when the measure rises above a second higher predetermined level, indicating that other components having a larger size are present. The other components may for examples be aggregates of the protein being collected.

The method may further comprise operating a valve to direct the eluate to a collection point when collecting the eluate. The method may thereby provide an automated way of collecting a desired portion of eluate, for example a portion in which a particular protein monomer is present before aggregates of the protein exceed a desired level within the eluate. The valve may for example be a switching valve, a fraction collector or flow diverter.

Embodiments of the invention allow for real-time, signal-based fraction collection or identity-based selective fractionation, and can be configured to operate automatically without user intervention during the collection process. The invention can thereby improve the efficiency of fraction collection of highly pure monomer isolates within biopharmaceutical formulations or protein/aggregate mixtures. Particular embodiments of the invention provide a solution to the above identified problems in biopharmaceutical manufacturing and protein purification applications.

Specific embodiments of the invention may involve independent and/or simultaneous use of static light scattering (SLS) and dynamic light scattering (DLS) data, with or without data from other detectors, to identify when a particular monomer begins and ends in the elution profile of a protein chromatogram. As well as the hardware for making such measurements, embodiments may incorporate software algorithms to facilitate automatic fraction collection and to simplify data interpretation. Particular embodiments may be in the form of a 'black-box' monomer detector which could be coupled with any protein purification system.

In accordance with a second aspect of the invention there is provided an apparatus for controlling collection of a sample of a liquid eluate from a separation process, the apparatus comprising:
  a light source configured to direct light to a portion of the liquid eluate;
  a detector configured to receive light from the light source scattered by suspended material in the liquid eluate;
  a sample collection outlet; and
  a computer configured to determine a measure of the suspended material derived from the detected scattered light and to direct flow of the liquid eluate towards the sample collection outlet when the measure is within a predetermined range and away from the sample collection outlet when the measure is outside of the predetermined range.

Various optional features relating to the first aspect of the invention may also be applied to the apparatus according to the second aspect.

DETAILED DESCRIPTION

The invention is described in further detail below by way of exemplary embodiments and with reference to the accompanying drawings, in which.

Like NMR and MS, described above, SLS and DLS detectors can provide identity information for fractionated species, respectively in the form of molecular weight and hydrodynamic size, but can do so more cost-effectively. More importantly, SLS and DLS can operate on liquid dispersions over a wide range of conditions and concentrations. Despite this, the coupling of chromatography with light scattering detectors is not a trivial one. By virtue of a progressively biased sensitivity for larger molecules, light scattering detectors are able to visualise molecules which are otherwise invisible to other detectors at low concentrations. Although this is undoubtedly advantageous for the detection of trace aggregate molecules, this hypersensitivity presents a methodological challenge when it precludes the detection of target molecules and/or affects data quality. These adverse effects are observed during column shedding, where the internal column packing material leaks into the detector and whose light scattering leads to elevated baselines, increased noise and decreased sensitivity. Other sources of contaminating scattered light can be found in running buffers and reservoirs, within tubing and adhered to column components. These contaminants are most commonly attributed to bacteria, insoluble particulate matter and dissolved gases, and manifest themselves as signal spikes during measurement. Such signal spikes can, however, be recognised during measurements due to their large difference from the desired signal, and can be either accounted for or removed from the data used to determine when collection should begin and end.

Figure 1:
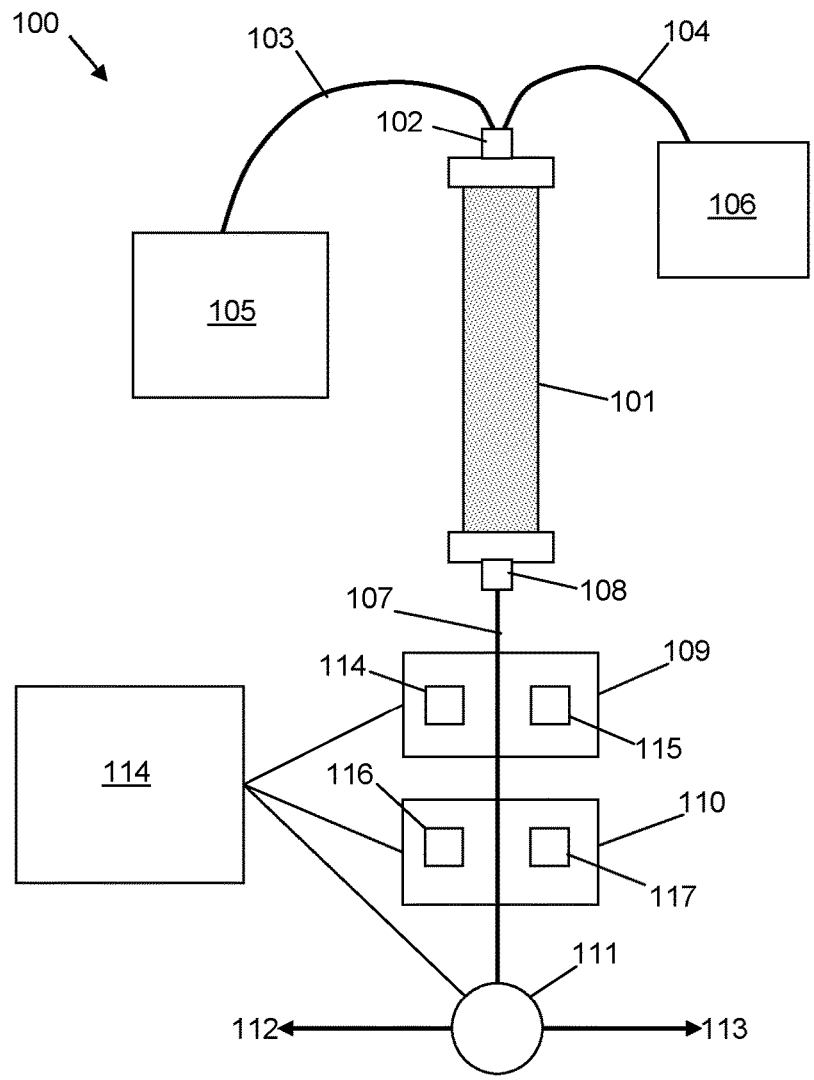
FIG. 1 is a schematic diagram of an apparatus in accordance with an embodiment of the invention.

The core components of a particular embodiment of the invention are illustrated schematically in the apparatus 100 shown in FIG. 1. The apparatus 100 comprises a chromatography column 101, an inlet 102 of which is connected via flow lines 103, 104 to a pumped source 105 of an eluent and a pumped source 106 of an analyte. An outlet flow line 107 is connected to an outlet 108 of the chromatography column 101. The outlet flow line passes eluate through first and second measurement modules 109, 110 and to a diverter valve 111. The diverter valve 111 is controllable to divert liquid passing through the flow line 107 selectively towards first and second collection points 112, 113. The first and second measurement modules 109, 110 and diverter valve 111, as well as the pumped sources 105, 106, may all be controllable by a suitably configured and programmed computer 114. The computer 114 is configured to control and receive measurement data from the measurement modules 109, 110, control the direction of flow of liquid via the diverter valve 111 and optionally also control the pumped sources 105, 106 to control the order and rate at which the analyte and eluent are passed through the chromatography column 101.

The first module 109 may be configured to measure a concentration of a compound in the eluate passing through the flow line 107, for example by way of absorption of ultraviolet light at a specific wavelength. The first module 109 may thereby comprise a first light source 114 and a first detector 115.

The second module 110 may be configured to measure scattered light from a compound in the eluate passing through the flow line 107, for example according to a static or dynamic light scattering technique. The second module 110 may thereby comprise a second light source 116 and a second detector 117, the second detector 117 configured to provide a signal to the computer 114 in response to light received from the second light source 116 via the flow line 107.

In certain embodiments the second module alone can be used for detecting an intensity of scattered light from suspended material in the eluate, from which a measure of the suspended material can be obtained to control collection of a portion of the eluate when the measure lies within a predetermined range. In other embodiments outputs from the first and second modules are used together to obtain the measure of the suspended material from which collection of the sample is controlled.

A sample of liquid analysed by the first and second modules may be considered to be a volume of liquid within the flow line 107 that is exposed to light from the first and second light sources 114, 116, from which measures of concentration and size of particles of the compound in the liquid may be determined. In the embodiment illustrated in FIG. 1 a given sample will pass first through the first module 109 and then through the second module 110 after a time delay dependent on the flow rate of liquid through the flow line 107. This time delay can be applied by the computer 114 to the measure of concentration obtained from the first module 109 when analysing measurement data to determine the size measure of the compound in the sample. The order in which the sample passes through the first and second modules may be reversed. In other embodiments the first and second modules may be coincident and configured to analyse a common sample volume at the same time, thereby removing the need for applying a time delay.

When coupling light scattering detection with chromatography and other separation technologies, it is important to mitigate the effects of light scattering contaminants (as identified above). This is particularly true in signal- and intensity-based fraction collection, as monomer/aggregate boundaries may be erroneously identified. The invention may use both physical and virtual strategies to minimise or offset the adverse effects of coupling with separation systems. One physical strategy is to use a physical filter situated in the flow line 107 after the chromatography column 101 (or other separating device) or immediately before the light scattering detector 110. A virtual strategy is to use digital filters and/or de-spiking algorithms to provide optimised data for real-time monitoring and fraction collection. In a general aspect therefore, the eluate may be filtered prior to exposing it to light from the light source. In addition, or alternatively, the measure of the suspended material derived from the detected scattered light may be processed to remove artefacts such as spikes.

Either SLS or DLS detection may be used to obtain real-time intensity signals during elution, which can be used by a software algorithm to monitor user-defined parameters such as a peak slope or a signal being above or below a particular threshold, which can be used to trigger or stop fraction collection. A user input is required only in order to set peak slope or intensity threshold values prior to fractionation. This is particularly advantageous for smaller scale applications, where calibration runs may be more difficult to apply.

SLS and DLS data may be used together with software algorithms to monitor a trend line that signals when a monomer peak begins and ends in a real-time elution profile of monomer/aggregate mixtures. The particular method used can adopt several different forms dependent on the type of data available to the software algorithm, but will generally encompasses numerical methods that exploit the non-linearity of light scattering signals and can be used independently and in combination with another linear detector. In one form of the invention, DLS data can be used independently to control fraction collection based on a trend line of the hydrodynamic size of eluting protein species.

In other embodiments, DLS and SLS data may be used concurrently to control fraction collection based on a trend line of the $I_{SLS}$/size ratio of detected species, i.e. the ratio of a measure of intensity of scattered light to a measure of size of particles in the eluate. The reciprocal ratio (size/$I_{SLS}$) may also be used and the term size could be converted to estimated molecular weight Mw based on a known size/Mw relationship for model proteins. In a general aspect therefore, a method in accordance with embodiments of the invention may involve beginning and ending collection of the sample when a measure of the suspended material in the eluate derived from the detected scattered light enters and leaves a predetermined range, wherein the measure of the suspended material is a ratio or inverse ratio of intensity of detected scattered light to a measure of size of particles of the suspended material.

In exemplary embodiments, data from a detector configured to determine concentration in combination with light scattering data is used to allow further identity-based parameters to control fraction collection. In other words, a measure of the suspended material may include a measure of intensity of light scattered by the suspended particles in the eluate and a measure of concentration of the suspended material in the eluate, the measures of intensity of scattered light and concentration being combined to obtain the measure of the suspended material. A concentration detector, based for example on UV, RI or fluorescence, can be used in conjunction with size or molecular weight (Mw) information obtained via light scattering to control fraction collection based on a combined measure that takes account of changes in apparent concentration as an elution profile varies during collection. The method described below relates to using a Mw trend line derived from SLS and UV signals to control fraction collection.

Figure 2:
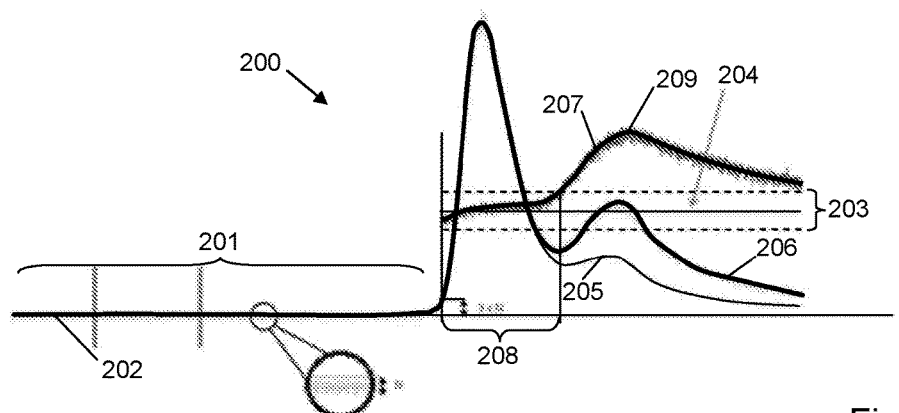
FIG. 2 is a plot of measures of UV absorbance and scattered light intensity over time, and a derived measure of molecular weight.

FIG. 2 illustrates an elution profile 200 of a protein monomer/aggregate mixture, depicting the use of a numerical tool for controlled fraction collection based on molecular weight. In an initial region 201, before any of the protein begins to elute from the column, a baseline 202 is determined, relative to which a threshold range 203 is set. A noise level N of the signal around this baseline 202 is measured. Once the signal rises to above a present multiple of the noise level N, for example 3N, a determination of whether molecular weight of the protein being collected begins, and a decision is made whether to collect the eluate. The concentration 205 and light scattering intensity 206 signals are combined in order to obtain a measure 207 of size of the suspended particles in the eluate, which in this case is a measure of molecular weight of the protein particles. Collection of the eluate is carried out during the collection period 208, which begins when the molecular weight signal 207 enters the predetermined range 203 and ends when the signal 207 leaves the range 203. During this collection period in the example shown the concentration signal 205 and light scattering intensity signal 206 largely overlap, but begin to diverge towards the end of the period. Following the collection period the molecular weight signal 207 rises to a peak value 209 corresponding roughly to a doubling of the molecular weight of the monomer protein and then falls away as the amount of protein present diminishes.

The molecular weight of the suspended particles can be obtained from concentration and light scattering data based on the Zimm equation, which can be approximated as:

$R_\phi \approx kMc$ where $R_\phi$ is the ratio of scattered to incident light intensity at an angle $\phi$ to the direction of incident light, M is the molecular weight of the dispersed particles, c is the concentration of the particles in the suspension and k is a constant dependent on the properties of the solvent, the wavelength of incident light and the angle of detection.

From the above equation it can be seen that if the concentration and scattered light intensities can be measured independently, a measure of molecular weight can be obtained, i.e. by rearranging the equation to give:

$$M \approx \frac{R_\phi}{kc}$$

The above relationship can be used to provide a relative measure of molecular weight, i.e. to determine when the average molecular weight of the dispersed particles changes, or an absolute measure when calibrated against a suspension of known molecular weight. In a general aspect therefore, the measure of the suspended material may be a measure of size of particles of the suspended material (which is related to molecular weight M), obtained by dividing the measure of intensity of scattered light by the measure of concentration. An advantage of this approach is that because the apparent concentration will vary throughout an elution profile, measuring the intensity of scattered light alone will not necessarily provide an accurate measure of the size of particles in the eluate at any given point. Taking the concentration into account therefore allows for a more accurate measure.

To calibrate the measure of molecular weight in order to obtain an absolute rather than relative value, a standard analyte of known molecular weight and concentration can be run, and elution times measured based on peaks of UV and LS signals. The different times at which the peaks are measured is stored as a time delay $\Delta t$. Instrument constants $K_{UV}$ and $K_{LS}$ are determined from the signals of concentration and molecular weight. A baseline region is determined, such that a least square fit to that region of data represents a valid baseline projection.

Following calibration, the following steps may be carried out as part of a process for fraction collection:

1. During elution, if the two light sources and detectors are at different points along the eluate flow line the concentration signal is shifted by the time delay $\Delta t$ as determined in calibration. The time delay may alternatively be calculated from a measure of flow rate in the flow line and the known distance between the concentration and light scattering detectors.
2. As elution time reaches the end of the baseline region, projected baselines for the concentration and light scattering channels are determined.
3. Over the baseline region a noise value N is determined, which is the greater of the peak-to-peak noise values for the concentration and light scattering signals.
4. Once the appropriate signal value is a present multiple of the noise signal above the baseline, for example 3N above the projected baseline, calculation of a molecular weight measure begins based on baseline-subtracted signals.
5. Collection of the eluate begins once the determined molecular weight is within a predetermined range, which may be defined by a range around a set molecular weight.
6. Once the molecular weight falls outside the predetermined range collection of the eluate ends.

The range of molecular weights may for example be determined according to a multiple of the standard deviation of determined molecular weight value. In the example shown in FIG. 2 the range 203 is preset to be +/−3 standard deviations about the predetermined molecular weight 204. Collection therefore stops once the signal 207 rises above the upper bound of the range 203. In a general aspect therefore, the predetermined range for defining the beginning and end of sample collection may be defined by a set deviation about a predetermined value of particle size or molecular weight. The set deviation may be a multiple of a standard deviation of the measured size or molecular weight.

The molecular weight trend line in the above example can constitute a measure of absolute molecular weight if the constant k is known beforehand. Alternatively, a trend line using apparent molecular weight can be used if the constant is set to 1 (or any arbitrary number) and only the relative change in molecular weight is used to signals the end of the monomer fraction collection. It is also possible that similar algorithms could direct fraction collection based on two identity parameters such as absolute Mw/size or apparent Mw/size ratios.

Figure 3:
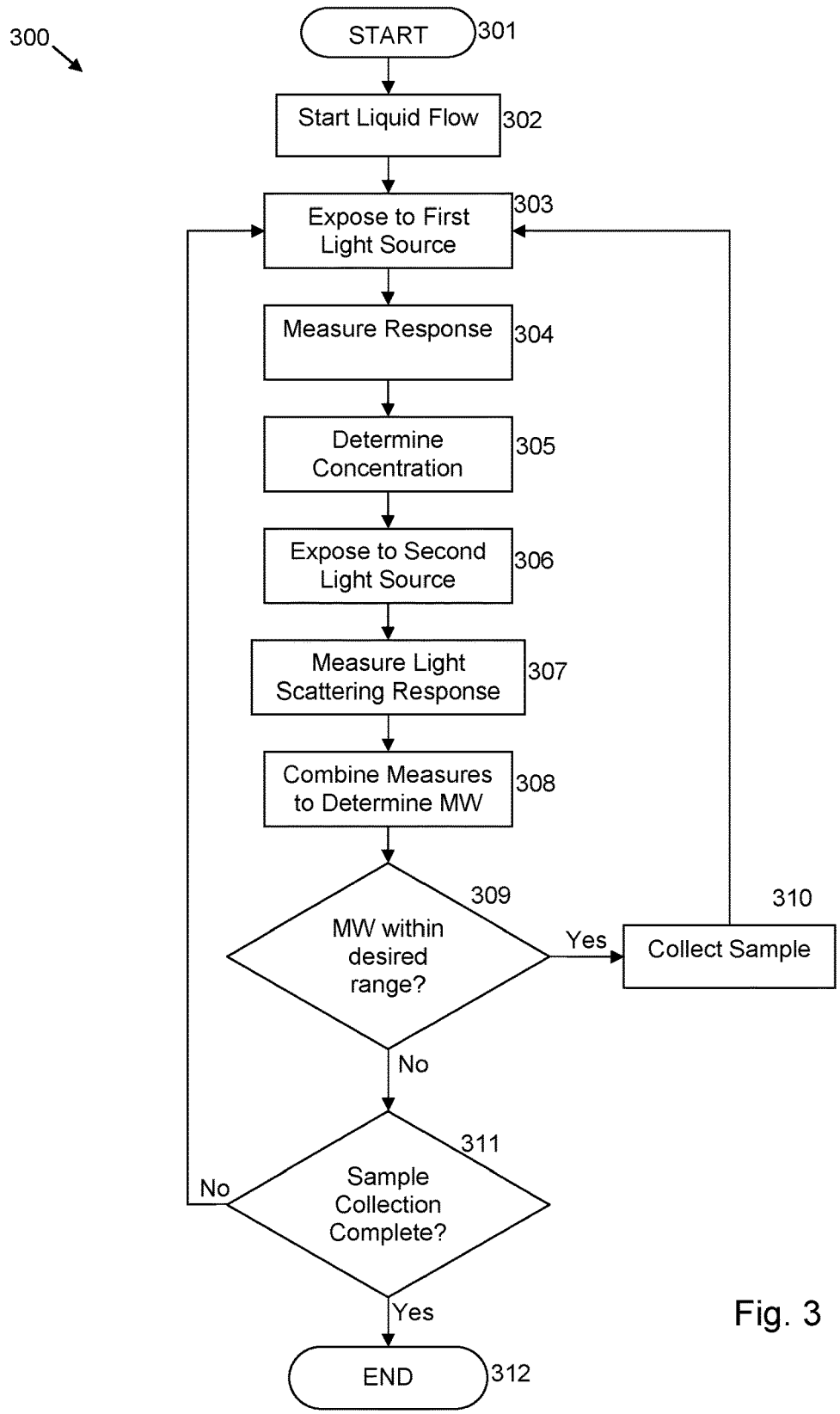
FIG. 3 is a flow diagram of a method according to an embodiment of the invention.

FIG. 3 illustrates schematically an exemplary method 300 according to an embodiment of the invention. The method begins at step 301, and liquid flow from the chromatograph is started (step 302). The sample in the flow line is exposed to a first light source (step 303) and a response is measured (step 304). A concentration is determined (step 305) from the measured response (step 305). The sample is then exposed to a second light source (step 306) and a light scattering response measured (step 307). The measures of concentration and light scattering are combined (step 308) to determine a measure of molecular weight. If the measure of molecular weight lies within a desired range, i.e. within the predetermined range of molecular weights (step 309), sample collection begins or is continued with (step 310). If the measure of molecular weight lies outside the predetermined range (step 309), and if sample collection is not complete or has not started (step 311), the method returns to step 303 as further sample flows through the flow line. If the measure of molecular weight lies outside the predetermined range (step 309) and sample collection is completed (step 311), the method finishes (step 312). Collection of data may continue once sample collection is complete, for example in order to provide data for post-collection analysis.

In alternative embodiments, steps 303 to 305 and 308 may be omitted, such that only a measure of light scattering response is used to determine the start and end points of sample collection.

In other alternative embodiments of the invention the concentration detector could be any other detector that allows selective monitoring of a property attributed to an eluting protein species. Such detectors may include atomic absorption or inductively coupled plasma technologies that selectively and quantitatively monitor biologically relevant elements, such as zinc, iron, calcium and copper, as well as pharmacologically relevant elements such as platinum; circular dichroism technologies that can monitor the level of secondary structure in protein species; Fourier-transform infrared (FT-IR) or Raman technologies that monitor the chemical composition of eluting protein species; UV photo diode array (PDA) or diode array detector (DAD) technologies that can simultaneously monitor the UV absorbance at two or more biologically relevant wavelengths; as well as other technologies listed in Table 1 above.

Further analysis may be performed on process data once acquired, for example to automatically identify and quantify monomer and aggregate peaks in elution profiles. The processed data could be sent to a report builder for automatic reporting or exported in a relevant format for use in other processes. Such processed data could be stored in a library or database and retrieved for automatic comparison, for example for profiling or number fingerprinting with a current dataset to provide information for QC and regulatory purposes, for example for use in assessing batch to batch variation; during method optimisation and in stability studies.

Using SLS and concentration data in a calibrated system, post collection processing may involve automatically finding a baseline in the collection data, selecting peaks in the data and assigning each peak to a monomer, dimer, aggregate etc.

Using DLS data can provide an alternative approach to automatic data processing. Size trend lines can be converted into estimated molecular weights based on known size/molecular weight relationships or user-defined relationships.

Using this information, a similar approach to that above could be implemented to identify and assign the aggregation state (monomer, dimer . . . n-mer etc.) of each peak.

The elimination of user intervention during data processing offers a significant advantage over existing technologies. This invention provides an opportunity for data to be routinely, robustly and reliably processed and automatically interpreted without user subjectivity, leading to a decrease in analyses times and cost, as well as user associated errors. According to theory, light scattering phenomena are inherently sensitive to size and/or Mw differences between monomers and aggregates. Therefore, by using light scattering parameters to define where monomer/aggregate elution boundaries occur the collection process can be made more sensitive. Increased sensitivity results in the elution of aggregates being detected earlier and fraction collection of the monomer is stopped or flow being diverted sooner, resulting in higher purity samples of the maximum possible yield.

The invention may be used in tandem with solution-based separations systems, which could include:
  Fast protein liquid chromatography (FPLC) systems
  High pressure liquid chromatography (HPLC) systems
  Ultra performance liquid chromatography (UPLC) systems
  Field flow fractionation (FFF) technologies
  Capillary electrophoresis (CE) technologies
Fractionation may be carried out using:
  Size-exclusion chromatography
  Ion exchange chromatography
  Affinity chromatography
  Membrane chromatography.

Fraction collection may be carried out by means of a fraction collector, a switching valve or another type of flow diverter.

Although the invention has been described in relation to aiding fraction collection and automated identification of protein monomers in predominantly protein purification applications, it is envisaged that the technology could be applied elsewhere. Other applications may include:
  Purification of vaccines, DNA and other polymers that have the potential to self-assemble.
  Purification of biosimilars.
  Fingerprinting of chromatographic profiles during quality control assessments or stability studies.
  One-step methodology to test the bio-engineering of aggregation-resistant antibodies.
  Purification of proteins that occur as functionally active natural aggregates from their functionally inactive counterparts.

A numerical approach may be used for automated oligomer detection in post-run data processing, for example for quality control purposes. An exemplary post-processing methodology may look for relationships between the signals of peaks in corresponding light scattering and concentration information obtained during elution. The following illustrative example outlines the approach that may be used when UV light is used for determining concentration. The relationship between the UV concentration and SLS signals of a monomer and dimer are well known, and can be described by Equations 1 to 6 below. Here, C is the concentration of the material under study; $I_{UV}$ and $I_{SLS}$ correspond to the intensity of the ultraviolet and static light scattering signal, respectively; dA/dc and do/dc correspond to the absorbance and refractive index increments, respectively; and $K_{UV}$ and $K_{SLS}$ correspond to detector constants. Parameters further annotated with subscript M denote variables corresponding to the monomer species and those annotated with subscript D correspond to the dimer species.

$$I_{UV} = K_{UV} \cdot (dA/dc) \cdot C \quad \text{Equation 1}$$

$$I_{SLS} = K_{SLS} \cdot (dn/dc) \cdot C \quad \text{Equation 2}$$

Since $(dA/dc)_M = dA/dc)_D$ and $C_D = 2 \cdot C_M$ then $$(dA/dc) \cdot K_{UV} = I_{UV,M}/C_M = I_{UV,D}/2 \cdot C_M \quad \text{Equation 3}$$

Simplified;

$$I_{UV,M} = I_{UV,D}/2 \quad \text{Equation 4}$$

Similarly $$Mw_M = Mw_D/2 \quad \text{Equation 5}$$

$$I_{SLS,D}/C_D = 2(I_{SLS,M}/C_M) \quad \text{Equation 6}$$

As the ratio of SLS to UV intensity of the dimer is twice that of the monomer (Equation 6), and the relationship of other aggregates are equally predictable, these relationships can be applied to acquired data and an oligomeric state, e.g. monomer, dimer, trimer . . . n-mer, assigned to the peaks in the elution profile.

There are two underlying assumptions of the data processing algorithm. A first is the any aggregated material in the sample mixture is composed only of the monomers in the mixture. A second is that the peak with the lowest SLS/UV peak ratio is the monomer.

An exemplary method for automatically assigning an oligomeric state to peaks in an elution profile may involve the following steps:

(1) Baselines are automatically fitted to the UV and SLS profiles.
(2) Automatic peak picking algorithms identify regions of the chromatograms where peaks are located.
(3) The UV and SLS peak areas are calculated.
(4) The ratio of SLS and UV areas for each identified peak are determined.
(5) The lowest SLS/UV ratio is identified and assigned as the 'monomer'.
(6) The oligomeric state of other peaks is calculated by dividing the given SLS/UV ratio by that of the SLS/UV ratio of the monomer peak. The oligomeric state is the integer value of this calculation—within a given tolerance threshold.
(7) Compositional analysis is given by the UV peak area of each peak.

Figure 4:
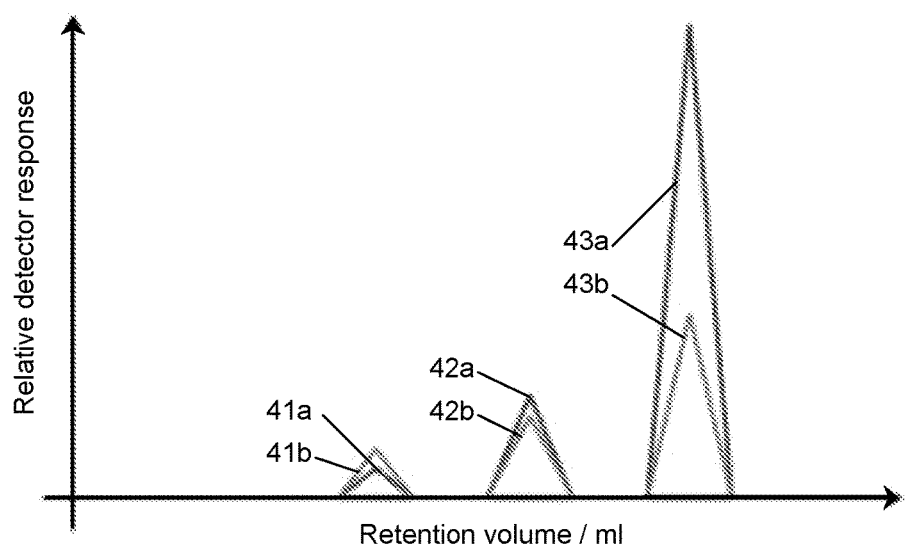
FIG. 4 is a simulated plot of an exemplary elution profile in the form of relative detector response for light scattering and concentration measurements as a function of retention volume.

An example for a theoretical dataset is provided in the table below and illustrated in FIG. 4, in which relative detector response (i.e. both concentration and light scattering intensity) is plotted as a function of retention volume, thereby representing the change in liquid eluate properties over a sample collection period. The peaks 41a, 42a, 43a for the UV concentration and the peaks 41b, 42b, 43b for the light scattering intensity are identified by their ratios as corresponding respectively to the trimer, dimer and monomer oligomeric states.

| UV Peak Area | 25.7 | 70.0 | 290.6 |
| SLS Peak Area | 29.5 | 54.2 | 116.1 |
| SLS/UV Ratio | 1.2 | 0.8 | 0.4 |
| Assignment | Trimer | Dimer | Monomer |

Similar approaches may be used for other types of secondary detectors for determining the oligomeric states. The SLS/UV ratio may for example be replaced by an SLS/C, $M_w$/UV or $M_w$/C ratio in the data processing algorithm.

In addition, the UV detector and UV data described in the above can be substituted with the information obtained from any concentration detector (i.e. this approach is not applicable when the second detector is a viscometer or mass spectrometer). In all instances the post-processing involves comparing signals of peaks in corresponding light scattering and concentration data.

Data processing in this way is clearly advantageous for quality control applications in biopharmaceutical manufacturing. The methodology could be further extended to report on batch to batch or lot to lot compositional variation.

In a general aspect therefore, a method for identifying components in a liquid eluate output from a separation process may comprise the steps of:

obtaining signal data from light scattering and concentration measurements taken of the liquid eluate during a sample collection period;
identifying one or more peaks in the light scattering and concentration signal data;
for each of the identified peaks, calculating a ratio between the light scattering and concentration signal data; and
identifying each peak as corresponding to an oligomeric state depending on the calculated ratio.

The method may be carried out on sample data obtained after or during the sample collection period.

Each peak may be identified as corresponding to a monomer, dimer, trimer or higher oligomeric state of a macromolecule, for example a protein.

Other embodiments are within the scope of the invention, which is defined by the appended claims.

The invention claimed is:

1. A method for identifying components in a liquid eluate output from a separation process, the method comprising:
obtaining signal data from light scattering and concentration measurements taken of the liquid eluate, the measurements taken during a sample collection period;
identifying two or more peaks in the light scattering and concentration signal data;
for each of the identified peaks, calculating a ratio between the light scattering and concentration signal data; and
identifying each peak as corresponding to one specific type of oligomer depending on the calculated ratio, wherein the specific types of oligomers comprise a monomer, a dimer, a trimer or a higher oligomeric state.

2. The method of claim 1, comprising obtaining a measure of a suspended material in the liquid eluate comprising obtaining a measure of intensity of light scattered by the suspended material and obtaining a measure of concentration of the suspended material, the measures of intensity of scattered light and concentration being combined to obtain the measure of the suspended material.

3. The method of claim 2 comprising exposing the liquid eluate to light from a first light source and a second light source, wherein the measure of concentration is derived from a response from the liquid eluate to the light from the second light source.

4. The method of claim 3 wherein the first and second light sources are arranged to illuminate a common sample volume.

5. The method of claim 3 wherein the first and second light sources are arranged to illuminate different portions of a flow line containing the liquid eluate.

6. The method of claim 3 wherein the second light source is an ultraviolet light source.

7. The method of claim 3 wherein the response from the liquid eluate is fluorescence in response to light from the second light source or attenuation of light from the second light source.

8. The method of claim 3 wherein the measure of the suspended material is a measure of size or molecular weight of particles of the suspended material obtained by dividing the measure of intensity of scattered light by the measure of concentration.

9. The method of claim 2 wherein the suspended material comprises monomers and aggregates of a protein.

10. The method of claim 2 wherein the sample collection period starts when the measure of the suspended material rises above a lower threshold of a predetermined range and ends when the measure rises above an upper threshold of the predetermined range.

11. The method of claim 2 wherein the sample collection period starts when the measure of the suspended material falls below an upper threshold of a predetermined range and ends when the measure falls below a lower threshold of the predetermined range.

12. The method of claim 2 wherein the sample collection period starts when the measure of the suspended material rises above a predetermined threshold and ends when the measure falls below the predetermined threshold.

13. The method of claim 2 wherein the sample collection period starts when the measure of the suspended material falls below a predetermined threshold and ends when the measure rises above the predetermined threshold.

14. The method of claim 1 wherein the separation process is chromatography, field flow fractionation or capillary electrophoresis.

15. The method of claim 1 further comprising operating a valve to direct the liquid eluate to a collection point.

* * * * *